United States Patent
Yoon et al.

(12)

(10) Patent No.: US 6,437,006 B1
(45) Date of Patent: Aug. 20, 2002

(54) PHARMACEUTICAL CARRIER FORMULATION

(75) Inventors: Joseph K. Yoon, Palisade Park, NJ (US); Richard W. Saunders, Palisades, NY (US); Mahdi Fawzi, Morristown, NJ (US)

(73) Assignee: American Cyanamid Company, Madison, WI (US)

( * ) Notice: Subject to any disclaimer, the term of this patent is extended or adjusted under 35 U.S.C. 154(b) by 77 days.

(21) Appl. No.: 09/668,970

(22) Filed: Sep. 25, 2000

Related U.S. Application Data
(60) Provisional application No. 60/228,813, filed on Sep. 27, 1999.

(51) Int. Cl.[7] ............... A61K 47/32; A61K 9/20; A61K 9/28; A61K 9/36; A61K 9/14
(52) U.S. Cl. .............. 514/772.5; 514/966; 424/464; 424/474; 424/480; 424/485
(58) Field of Search ............... 514/772.5, 966; 424/464, 474, 480, 465

(56) References Cited

U.S. PATENT DOCUMENTS

| | | | |
|---|---|---|---|
| 4,578,391 A | 3/1986 | Kawata et al. | |
| 4,620,974 A | 11/1986 | Hersh et al. | |
| 4,744,988 A | 5/1988 | Brox | |
| 5,356,904 A | 10/1994 | Freidinger et al. | |
| 5,516,774 A | 5/1996 | Albright et al. | |
| 5,525,614 A | 6/1996 | Blankley et al. | |
| 5,641,512 A | 6/1997 | Cimiluca | |
| 5,654,297 A | 8/1997 | Albright et al. | |
| 5,686,445 A | 11/1997 | Albright et al. | |
| 5,700,796 A | 12/1997 | Albright et al. | |
| 5,719,278 A | 2/1998 | Albright et al. | |
| 5,856,564 A | 1/1999 | Tanaka et al. | |
| 6,120,802 A | * 9/2000 | Breitenbach et al. | ....... 424/464 |

FOREIGN PATENT DOCUMENTS

| | | |
|---|---|---|
| EP | 0514667 | 11/1992 |
| EP | 0815854 | 1/1998 |
| WO | 9519579 | 7/1995 |
| WO | 9640071 | 12/1996 |
| WO | 9641622 | 12/1996 |
| WO | 9824430 | 6/1998 |
| WO | 9936060 | 7/1999 |

OTHER PUBLICATIONS

Shah et al., Bull. Tech/Gattefosse Rep., 1996, 89, 27–38.

* cited by examiner

*Primary Examiner*—Thurman K. Page
*Assistant Examiner*—Blessing Fubara
(74) *Attorney, Agent, or Firm*—Michael R. Nagy

(57) ABSTRACT

This invention provides carrier systems useful in preparing pharmaceutical formulations, the systems comprising, by weight percentage, from about 1% to about 20%, preferably from about 5% to about 12%, of a surfactant component; from about 55% to about 93%, preferably from about 60% to about 85%, of a component of one or more polyethylene glycols (PEG); and from about 1% to about 25%, preferably from about 5% to about 15%, of one or more sucrose fatty acid esters or polyvinylpyrrolidone (PVP) with a K value between about 15 and about 90, preferably with a K value of from about 16 to about 18, most preferably about 17, as defined in USP/NF, or a combination of one or more sucrose fatty acid esters or PVP, and, optionally, one or more pharmaceutically acceptable preservatives or antioxidants, such as BHA, BHT, ascorbyl palmitate or benzyl alcohol.

14 Claims, No Drawings

PHARMACEUTICAL CARRIER FORMULATION

This application claims the benefit of U.S. Provisional Application No. 60/228,813 Sep. 27, 1999, which was converted from U.S. patent application No. 09/406,164, filed Sep. 27, 1999, pursuant to a petition filed under 37 C.F.R. 1.53(c)(2)(i).

This applications concerns new formulations for pharmaceutical carriers, excipients or pharmaceutical media which are useful in formulating pharmaceutical compositions for biologically active compounds having poor oil and water solubility and/or poor biological absorption properties. The invention particularly relates to orally administered formulations of these compounds.

BACKGROUND OF THE INVENTION

The art describes many methods of producing liquid or semi-solid encapsulated pharmaceutical formulations. In Bull. Tech./Gattefosse Rep. (1996), 89, 27–38, authors Shah et al. describe hard gelatin capsule technology, particularly for use in enhancing the bioavailability of poorly soluble or poorly absorbed drugs.

U.S. Pat. No. 4,620,974 (Hersh et al.) teaches a hard gelatin capsule comprising a telescoping two-piece cap with a lubricant comprising a polyethylene glycol of a molecular weight between about 200 and about 900 present in admixture with the composition at a concentration of from about 0.5 to about 25 weight percent.

WO 96/40071 (Lamberti) discloses methods and devices for producing minimal volume capsules. WO 96/41622 (Tanner et al.) teaches suspensions suitable for encapsulation in gelatin capsules, particularly including a solid phase of solid particles and a liquid phase capable of suspending the solid phase.

U.S. Pat. No. 5,641,512 (Cimiluca) teaches soft gelatin encapsulated analgesics in which the shell contains a xanthine derivative, such as caffeine.

EP 0 815 854 A1 discloses a substantially translucent, semi-solid fill material for a soft gelatin capsule, the semi-solid material being sufficiently viscous that it cannot be expelled from the capsule with a syringe at room temperature.

U.S. Pat. No. 4,744,988 (Brox) teaches soft gelatin capsules comprising a shell of gelatin, a softener and a filling of a polyethylene glycol and a low polyhydric alcohol and at least one active substance, characterized in that the shell contains 4 to 40 percent sorbital or sorbitanes, at least half of the weight of polyethylene glycol used is a polyethylene glycol having a mean molecular weight of 600, and the capsule filling comprises up to 20% by weight of glycerol and/or 1,2-propylene glycol.

WO 95/19579 (Dhabhar) teaches a process for solubilizing difficulty soluble pharmaceutical agents in a mixture of polyethylene glycol and propylene glycol by using a polyvinylpyrrolidone with a specific viscosity average molecular weight of from about 5,000 to about 25,000.

U.S. Pat. No. 4,578,391 (Kawata et al.) describes oily compositions for antitumor agents comprising at least one sparingly oil soluble or water-soluble antitumor drug, at least one fat or oil, and at least one solubilizing adjuvant in an oily vehicle, selected from crown ether, lecithin, polyethylene glycol, propylene glycol, vitamin E, polyoxyehtylene alkylether, and sucrose esters of fatty acids.

WO 98/24430 (Gautier et al.) teaches an anhydrous solubilizing/stabilizing system, emulsifiable or microemulsifiable in water, for solubilizing hydrophobic N-sulphonyl indolin derivatives of the structure:

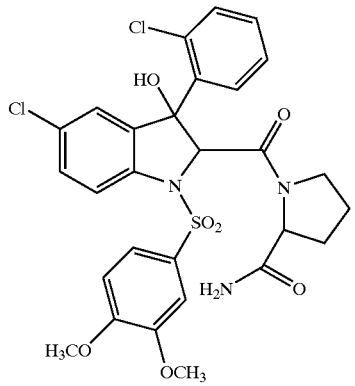

U.S. Pat. No. 5,356,904 (Freidinger et al.) discloses methods of using oxytocin antagonist compounds of the formulae:

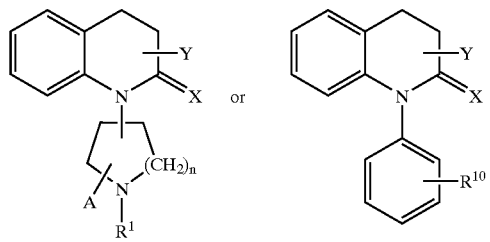

WO 95/03305 discloses nitrogenous aromatic 5-membered fused benzazepine derivatives, having the structure below, which are pharmacologically useful as arginine vasopressin antagonists.

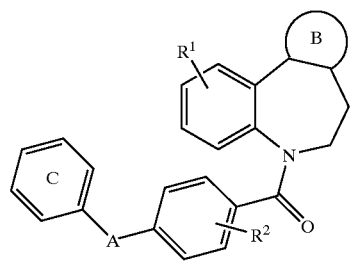

EP 0 514 667 B1 (Ogawa et al.) teaches benzazepine derivatives of the

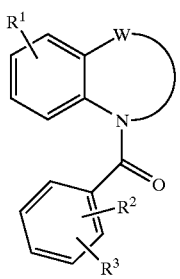

as vasopressin antagonists useful as vasodilators, hypotensive agents, water diuretics and platelet agglutination inhibitors.

U.S. Pat. No. 5,525,614 (Blankley et al.) teaches substituted 1,2,3,4-tetrahydroisoquinolines, having the general structure below:

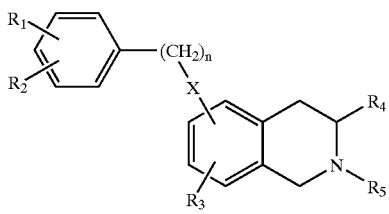

as having angiotensin II receptor antagonist properties and as effective in treating disorders related to excessive vasopressin secretion.

U.S. Pat. No. 5,516,774 (Albright et al.) teaches tricyclic vasopressin compounds, including those having a pyrrolobenzodiazepine core. U.S. Pat. Nos. 5,700,796 and 5,719,278 provide other tricyclic benzazepine compounds useful as vasopressin antagonists. U.S. Pat. No. 5,654,297 teaches vasopressin antagonists having bicyclic non-peptide cores and U.S. Pat. No. 5,686,445 discloses similarly active compounds having pyridobenzoxazapine and pyridobenzothiazepine core structures.

SUMMARY OF THE INVENTION

This invention provides new pharmaceutical carrier or excipient systems useful in the formulation of biologically active compounds and formulations produced using the carrier system, as well as processes for producing the carrier systems and formulations. Of particular interest is the use of the novel carrier systems in the formulation of encapsulated oral pharmaceutical compositions for mammalian use, preferably for human use.

In general, the carrier systems of this invention comprise, by weight percentage, a composition having the components:

a) from about 1% to about 20%, preferably from about 5% to about 12%, of a surfactant component;

b) from about 55% to about 93%, preferably from about 60% to about 85%, of a component of one or more polyethylene glycols (PEG) with an average molecular weight range of from about 190 to about 3450, preferably 400 to 1540; and c) from about 1% to about 25%, preferably from about 5% to about 15%, of one or more sucrose fatty acid esters or polyvinylpyrrolidone (PVP) with a K value between about 15 and about 90, preferably with a K value of from about 16 to about 18, most preferably about 17, as defined in USPINF, or a combination of one or more sucrose fatty acid esters or PVP.

The polyethylene glycol component may be comprised of one or more PEG polymers, preferably commercially available PEG polymers between PEG 200 and PEG 4,000, i.e. those PEG polymers having an average molecular weight between about 190 and about 4800. More preferred are PEG polymers between average molecular weights of from about 190 to about 3450, most preferably between about 400 and 1540. Among the preferred PEG polymers are PEG 400, having an average molecular weight between about 380 and about 420, and PEG 1,000, having an average molecular weight between about 950 and about 1050. The ratio of high and low molecular weight PEG species within the PEG component is preferably from about 2.5:1 to about 1:2.5, more preferably about 1:1. As an example, a preferred blend of PEG polymers within this invention would include a 1:1 blend of PEG 400 and PEG 1000. It may be preferable to choose a mixture of PEG components which will have a melting point at or near the physiological temperature of the mammal to receive the formulation. Mixtures of final components which have a viscosity range of from about 140 to about 1500 centipoise at 37° C. may be preferred, more preferably a range of from 300 to about 800 centipoise at 37° C.

The surfactants that may be used with the present formulations include, but not limited to, polysorbate 20 (polyoxyethylene 20 sorbitan monolaurate), Polysorbate 60, Polysorbate 40, polysorbate 80, Span 80 Sorbitan Oleate, a product of ICI Americas, Wilmington, Del., polysorbate 81, polysorbate 85, polysorbate 120, bile acids and salts defined by Martindale The Extra Pharmacopoeia Thirtieth Edition on page1341–1342 such as Sodium taurocholates, Sodium deoxytaurocholates, Chenodeoxycholic acid, and ursodeoxycholic acid, and pluronic or poloxamers such as Pluronic F68, Pluronic L44, Pluronic L101, or combinations of one or more of the above. Polysorbate 80, by itself or in combination with one or more other surfactants, is preferred for use with this invention.

The sucrose fatty acid esters useful with this invention include those commercially available and art recognized esters useful for orally administered pharmaceutical compositions, including monoesters, diesters and triesters of sucrose, or mixtures or blends thereof. Specific examples of esters useful with this invention are sucrose monolaurate, sucrose monomyristate, sucrose monopalminate, sucrose monostearate, sucrose distearate, sucrose tristearate, sucrose trimyristate, and sucrose tripalmitate, or combinations thereof.

In addition to these components, other enhancing or protective pharmaceutically acceptable antioxidants or preservatives may be added to the compositions of this invention, preferably accounting for from about 0.1% to about 4% by weight of the composition, more preferably from about 0.1% to about 3% of the composition. Examples may include ascorbyl palmitate, benzyl alcohol, butylated hydroxyanisole (BHA), butylated hydroxytoluene (BHT), etc. Examples of these components in the present formulations would include BHA at a concentration from about 0.3% to about 2.5% (% w/w) and BHT at a concentration from about 0.005% to about 0.15% (% w/w), preferably with a mixture of BHA and BHT within these ranges.

One embodiment of a pharmaceutically useful carrier or excipient system of this invention comprises, as compared by % weight/weight:

a) from about 32% to about 36% of PEG 1000;

b) from about 35% to about 46% polyethylene glycol 400 (PEG 400).

c) from about 9% to about 14% of povidone;

d) from about 9% to about 14% Polysorbate 80;

e) from about 0.005% to about 0.02% butylated hydroxytoluene (BHT); and f) from about 0.5% to about 2.0% Butylated Hydroxyanisole (BHA).

In instances where a greater amount of antioxidant or preservative activity is desired, the percentages of the BHT and BHA in components e) and f) can understandably be increased relative to each other to create an antioxidant/preservative component of up to about 4%.

It will be understood that the percentages of the compounds in each of the formulations of these carrier or excipient systems will equal 100%, without taking into account an active pharmacological agent or other pharmacological components, such as coloring agents, fillers, pharmaceutically acceptable adjuvants, encapsulating or coating components, etc. In a preferred embodiment of this invention, the carrier system above is combined with a pharmacologically active agent and then encapsulated, such as with a hard or soft gelatin capsule.

Another preferred embodiment of this invention includes a carrier or excipient system useful for pharmaceutical compositions comprising on a weight per weight percentage basis:

a) from about 33% to about 35% of PEG 1000;
b) from about 37.5% to about 43% polyethylene glycol 400 (PEG 400);
c) from about 10.5% to about 13% Polysorbate 80;
d) from about 0.075% to about 0.015% butylated hydroxytoluene (BHT);
e) from about 0.75% to about 1.5% Butylated Hydroxyanisole (BHA); and
f) from about 10.0% to about 13% of povidone.

The carrier or excipient systems of this invention may be used to formulate pharmaceutical compositions for numerous classes of compounds. These include those chemical compounds produced around various bicyclic and tricyclic core molecules, including bi- and tricyclic heterocycles. Examples of the compounds in question include those disclosed in U.S. Pat. Nos. 5,516,774; 5,654,297; 5,686,445; 5,700,796; and 5,719,278, each of which is fully included herein by reference. Also incorporated herein by reference for use with the present carrier systems are the compounds disclosed in WO 98/24430 (Gautier et al.), U.S. Pat. No. 5,356,904 (Freidinger et al.), WO 95/03305, EP 0 514 667 B1 (Ogawa et al.), and U.S. Pat. No. 5,525,614 (Blankley et al.), each mentioned above in the Background of the Invention.

Of specific interest as an active pharmaceutical ingredient or agent for use with the present invention is for N-[4-(5H-pyrrolo[2,1-c][1,4]benzodiazepin-10(11H)ylcarbonyl)-3-chlorophenyl]-5-fluoro-2-methylbenzamide, also known as VPA-985, or the pharmaceutically acceptable salts thereof, which has the structure:

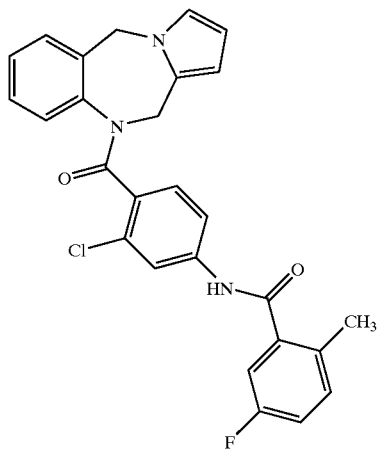

VPA-985 is a V2 receptor antagonist (vasopressin antagonist) with the ability to elicit the removal of water in mammals, without the excretion of necessary electrolytes. The synthesis of this compound and its salts is disclosed in U.S. Pat. No. 5,516,774 (Albright et al.), which is incorporated herein by reference.

Also among the most preferred compounds for use as an active ingredient with the carrier or excipient formulations of this invention is [2-Chloro-4-(3-methyl-pyrazol-1-yl)-phenyl-(5H, 11H)-pyrrolo[2,1-c][1,4]benzodiazepin-10-yl)-methano, or pharmaceutically acceptable salts thereof, having the structure:

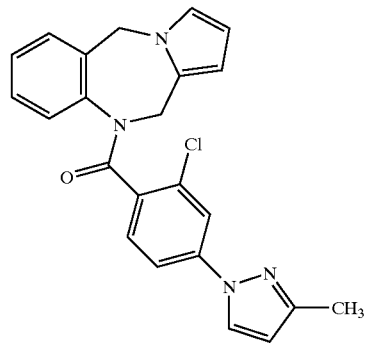

Formulations using this compound are useful in methods for treating in humans or other mammals diseases, conditions or disorders in which vasopressin agonist activity is desired. These methods of treatment include those for diseases, conditions or disorders which make it desirable to release factor VIII and von Willebrand factor into the circulatory system, release tissue-type plasminogen activator (t-PA) in the blood circulation, or affect the renal conservation of water and urine concentration. Such methods of treatment include, but are not limited to, treatments for diabetes insipidus, nocturnal enuresis, nocturia, urinary incontinence, or bleeding and coagulation disorders in humans or other mammals, including hemophilia. The methods herein for which the formulations may be used also include facilitation in humans or other mammals of temporary delay of urination, which may also be described as controlling or treating the inability to temporarily delay urination, whenever desirable. This method is understood to include treatments facilitating the temporary delay of urination which are separate from and not included in the treatment of the conditions known as nocturnal enuresis and nocturia.

This compound has been synthesized by the steps described below.

(2-Chloro-4-fluorophenyl)-(5H, 11H-pyrrolo[2,1-c][1,4]benzodiazepin-10yl)-methanone Oxalyl chloride (2.60 g) was added to a suspension of 2-chloro-4-fluorobenzoic acid (3.44 g) in dichloromethane (50 ml). Two drops of dimethylformamide were added and the mixture was stirred for 18 hours at room temperature. The resultant solution was evaporated to give the crude 2-chloro-4-fluorobenzoyl chloride as a viscous oil (3.72 g).

The crude 2-chloro-4-fluorobenzoyl chloride (3.68 g) in dichloromethane (25 ml) was added portionwise to a stirred, ice cooled solution of 10,11-dihydro-5H-pyrrolo[2,1-c][1,4]benzodiazepine (2.76 g), diisopropylethylamine (2.47 g) and dichloromethane (50 ml). After 18 hours at room temperature, the reaction mixture was washed with water and saturated aqueous sodium bicarbonate. The dichloromethane solution was dried with anhydrous sodium sulfate and filtered through a short column of hydrous sodium magnesium silicate and further eluted with several volumes of dichloromethane. The combined organic phase was concentrated on a hot plate with the gradual addition of hexane until crystallization occurred. After cooling, the crystals were collected by filtration to yield the title compound (3.85 g), m.p. 110–112° C.

[2-Chloro-4-(3-methyl-pyrazol-1-yl)-phenyl]-(5H, 11H)-pyrrolo[-2,1-c][1,4]benzodiazepin-10-yl)-methanone (Isomer A) and [2-Chloro-4-(5-methyl-pyrazol-1-yl)-phenyl]-(5H,11H)-pyrrolo[2,1-c][1,4]benzodiazepin-10-yl)-methanone (Isomer B)

Method 1 To 60% sodium hydride in oil (0.3 g, degreased with hexane) dimethylformamide (25 ml) was added 3-methylpyrazole (0.55 g). When the drogen evolution subsided, (2-chloro-4-fluorophenyl)-(5H,11H-pyrrolo[2,1-c][1,4]benzodiazepin-10-yl)-methanone (1.70 g) was added. The reaction mixture was heated for 18 hours in a sand bath (internal temperature 125° C.). The reaction mixture was then poured onto ice and further diluted with a saturated saline solution. The precipitated solid was recovered by filtration. The crude product was dissolved in dichloromethane, dried over anhydrous sodium sulfate, and then filtered through a short column of hydrous sodium magnesium silicate and further eluted with several volumes of dichloromethane. The combined eluate was refluxed on a hot plate with the gradual addition of hexane until an opaque solution was observed. On cooling an amorphous solid was obtained. On subjecting this material to a second column of hydrous sodium magnesium silicate and evaporation of the solvent in vacuo gave a mixture of regioisomers 9A and 9B in approximately a 9:1 ratio as an amorphous glass (1.11 g), MS, m/z: 403.2 (M+H)$^+$.

Method 2: To a pre-cooled, stirred suspension of hexane-washed 60% sodium hydride (3.00 g) in dry dimethylformamide (250 ml) was added dropwise under nitrogen 3-methylpyrazole (5.50 g) at 0° C. The mixture was warmed to room temperature. After gas evolution ceased, 2-chloro-4-fluorophenyl)-(5H,11H-pyrrolo[2,1-c][1,4]benzodiazepin-10-yl)-methanone (17.0 g) was added as a solid, and the mixture heated to 130° C. for one hour. The reaction mixture was poured into ice water, a precipitate collected by filtration, and air-dried. The precipitate was dissolved in dichloromethane, dried over anhydrous sodium sulfate, and filtered through a short column of silica gel, eluting with ethyl acetate. The combined filtrate was evaporated in vacuo to a residual foam (18.5 g). Purification and separation of regioisomers by low pressure column chromatography on silica gel eluting with a gradient mixture of ethyl acetate-hexane (10:90 to 25:75), yielded two purified regioisomers:

Isomer A, [2-chloro-4-(3-methyl-pyrazol-1-yl)-phenyl]-(5H,11H)-pyrrolo-[2,1-c][1,4]benzodiazepin-10-yl)-methanone (13.5 g), as a colorless amorphous solid; MS (EI), m/z: 402 (M)$^+$. A sample (0.5 g) was crystallized from diethyl ether, followed by recrystallization from ethanol to yield regioisomer A (0.275 g) as a colorless, crystalline solid, m.p. 141–143° C.;

Isomer B, [2-chloro-4-(5-methyl-pyrazol-1-yl)-phenyl]-(5H,11H)-pyrrolo[2,1-c][1,4]benzodiazepin-10-yl)-methanone (1.93 g) as a colorless amorphous solid. A sample was crystallized from diethyl ether, followed by recrystallization from methanol to yield regioisomer B as colorless, needles (1.4 g), m.p. 160–163° C.; MS (EI), m/z: 402 (M)$^+$, MS (+FAB), m/z: 403 (M+H)$^+$.

In order to obtain consistency of administration, it is preferred that a composition of the invention is in the form of a unit dose. Suitable unit dose forms preferably include tablets or capsules, though one skilled in the art will understand semi-solids or gels of this invention are also readily made and useful. Such unit dose forms may contain from 0.1 to 1000 mg of an active ingredient compound of the invention and preferably from 2 to 50 mg. Still further preferred unit dosage forms contain 5 to 25 mg of a pharmaceutically active compound of the present invention. The formulations of the present invention can be administered orally at a dose range of about 0.01 to 100 mg/kg of active ingredient or preferably at a dose range of 0.1 to 10 mg/kg of active ingredient. Such compositions may be administered from 1 to 6 times a day, more usually from 1 to 4 times a day.

The compositions of the invention may be formulated with other conventional carriers or excipients such as fillers, disintegrating agents, adjuvants, binders, lubricants, flavoring agents and the like.

Preferably, the formulations of this invention are enclosed in a sealed enclosure after manufacture, such as soft or hard gelatin capsules. The formulations of this invention may be created as a liquid or semi-liquid formulation and introduced into a capsule. Similarly, using an acceptable range of components and/or temperatures, the formulation may be made as a gel or solid prior to encapsulation.

The carrier system of this invention may also be used in pharmaceutical compositions containing as active pharmaceutical agents or ingredients other poorly soluble compounds including, but not limited to, the compounds disclosed in EP 0709386 (Yamanouchi Pharmaceutical Company, Ltd), including the compound N-[1,1'-biphenyl]-2-yl-4-[(4,5-dihydro-2-mehtylimidazo[4,5-d][1]benzazepin-6(1H)-yl)carbonyl]-benzamide (CAS Reg. No. 179528-39-3 YM 087), or pharmaceutically acceptable salts thereof.

Processes for Preparing Pharmaceutical Formulations

This invention also includes methods for producing the formulations using the biologically and pharmacologically active ingredients of the type described herein. A process of this invention comprises the steps of:

a) combining, preferably with mixing or stirring, the PEG and surfactant components to create a first carrier mixture;

b) raising the temperature of the first carrier mixture to a range of from about 75° C. to about 95° C., preferably from about 80° C. to about 90° C.;

c) adding the active pharmacological ingredient or agent to create a first pharmaceutical composition mixture;

d) stirring the first pharmaceutical composition mixture, preferably with heating, until the first pharmaceutical composition mixture is clear, preferably at a temperature from about 115° C. to about 170° C., more preferably at a temperature from about 130° C. to about 150° C., most preferably at a temperature from about 135° C. to about 145° C.;

e) cooling the first pharmaceutical composition, if necessary, to a temperature of from about 75° C. to about 95° C., preferably from about 80° C. to about 90° C.;

g) adding the amount of sucrose fatty acid ester(s) and/or povidone to create a final pharmaceutical composition mixture, preferably with stirring until the final pharmaceutical composition mixture is clear.

In cases wherein optional antioxidants or preservatives are used, such as BHA, BHT, etc., the following steps may be employed:

a) combining, preferably with mixing or stirring, the PEG component (such as a mixture of PEG 400 and PEG 1000) and the surfactant component (such as Polysorbate 80) to create a first carrier mixture;

b) raising the temperature of the first carrier mixture to a range of from about 75° C. to about 95° C., preferably from about 80° C. to about 90° C.;

c) adding to the first carrier mixture optional antioxidant or preservative components to create a second carrier mixture, which is then stirred or otherwise mixed until the second carrier mixture is a clear solution;

d) adding the active ingredient to create a first pharmaceutical composition mixture;

e) stirring the first pharmaceutical composition mixture, preferably with heating, until the first pharmaceutical composition mixture is clear, preferably at a temperature of from about 115° C. to about 170° C., more preferably at a temperature from about 130° C. to about 150° C., most preferably at a temperature from about 135° C. to about 145° C.;

f) optionally cooling the first pharmaceutical composition to a temperature of from about 75° C. to about 95° C., preferably from about 80° C. to about 90° C;

g) adding the amount of sucrose fatty acid ester(s) and/or povidone to create a final pharmaceutical composition mixture, preferably with stirring until the final pharmaceutical composition mixture is clear.

One skilled in the art will understand the viscosity and form of the final formulation may be manipulated with components within the scope of this invention and temperature ranges during processing. For instance, a fluid or semi-solid composition may be produced with the more fluid PEG, surfactant and PVP species within the scope of this invention. More gel-like, viscous or semi-solid compositions may be produced with combinations of higher molecular weight PEG components and PVP components having higher K values. Moreover, the components may be cooled below their melting point if milling or other processing of the final composition is desired. To create a more pelletized initial composition, a fluid composition of this invention may be sprayed onto a cooled Teflon®-coated surface to form small solid spheres, which may be individually coated or collected for further processing.

Specific non-limiting examples of formulations within the scope of this invention are provided below, using the compound of N-[4-(5H-pyrrolo[2,1-c][1,4]benzodiazepin-10(11H)ylcarbonyl)-3-chlorophenyl]-5-fluoro-2-methylbenzamide (VPA-985) as a non-limiting illustrative example. It is understood that comparable formulations may be produced using other active ingredients, or combinations thereof.

EXAMPLE 1

50 mg/Capsule: Oral Formulation at 10% Drug Loading

In place of the polysorbate 80 in this formulation of Example 1, other polysorbate series such as Tween 20, 40 and 60 can also be used, alone or in combination with each other and/or polysorbate 80.

|  | (% w/w) | per capsule (mg) | 20,000 capsule batch (g) |
|---|---|---|---|
| active ingredient | 10.42 | 50.00 | 1000.00 |
| Inactive Ingredients: |  |  |  |
| PEG 1000, NF | 30.96 | 148.61 | 2,972.16 |
| Povidone USP K-17 | 10.00 | 48.00 | 960.00 |
| Polysorbate 80, NF | 10.00 | 48.00 | 960.00 |
| BHT, NF | 0.09 | 0.42 | 8.32 |
| BHA, NF | 0.87 | 4.16 | 83.2 |
| PEG 400, NF[2] | Q.S. to 100 | Q.S. to 480.00 | Q.S. to 9,600 |

1. Weigh the Polysorbate 80, PEG 400, and PEG 1000 into a suitable mixing vessel, stir using a top mounted mixer, and warm to 85±5° C.

2. Add BHT and BHA to the mixing vessel, very slowly to prevent formation of lumps. Continue stirring at 85±5° C., until a clear solution was formed.

3. Add active ingredient to the vessel at 85±5° C., very slowly to prevent formation of lumps. Slowly raise the temperature to 125±5° C., and stir until the active ingredient dissolves completely.

4. Cool the solution in step 4. to 60±5° C.

5. Add Povidone, USP, K-17 (Plasdone C-15, ISP) slowly to step 5, to prevent the formation of lumps.

Let the solution warm up to 85±5° C. Stir until the solution becomes clear.

6. Encapsulate 480 mg of the finished solution (in step 10) into size 1 capsules at 38±5° C., such as by using a Hoglinger and Karg (H&K) 800L encapsulator machine. During encapsulation cool the body of capsule using cool Nitrogen, which was passed through dry ice.

7. Band seal the capsules with gelatin solution.

EXAMPLE 2

50 mg/Capsule: Oral Formulation at 10% Drug Loading

In place of surfactant used in this formulation (poloxamer 188), other polymers in the series such as Pluronic L44, Pluronic L101 can also be used.

|  | (% w/w) | per capsule (mg) | 20,000 capsule batch (g) |
|---|---|---|---|
| active ingredient | 10.42 | 50.00 | 1000.00 |
| Inactive Ingredients: |  |  |  |
| Povidone USP K-17 (Plasdone C-15, ISP) | 10.00 | 48.00 | 960.00 |
| Poloxamer 188, NF | 12.00 | 57.60 | 1152.00 |
| BHT NF | 0.09 | 0.42 | 8.32 |
| BHA NF | 0.87 | 4.16 | 83.20 |
| PEG 400 NF | Q.S. to 100 | Q.S. to 480.00 | Q.S. to 9600 g |

This formulation is manufactured the same as that of the formula of Example 1 (50 mg/capsule) with the exception that 12% of poloxamer was used in place of the polysorbate 80 in this formulation. The encapsulation weight is 480 mg.

EXAMPLE 3

50 mg/Capsule

Example 4 provides a formulation with a combination of two or more surfactants.

|  | (% w/w) | per capsule (mg) | 20,000 capsule batch (g) |
|---|---|---|---|
| active ingredient | 10.64 | 51.07 | 1,021.44 |
| Inactive Ingredient: |  |  |  |
| PEG 1000, NF | 28.60 | 137.28 | 2,745.60 |
| Povidone USP K-17 (Plasdone C-15, ISP) | 10.00 | 48.00 | 960.00 |
| Polysorbate 40, NF | 5.00 | 24.00 | 480.00 |
| Poloxamer 188, NF | 10.00 | 48.00 |  |
| BHT, NF | 0.09 | 0.43 | 8.64 |
| BHA, NF | 0.87 | 4.18 | 83.52 |
| PEG 400, NF | Q.S. to 100 | Q.S. to 480.00 | Q.S. to 9600.00 |

The formulation of Example 3 is manufactured the same as that of Example 1 (50 mg/capsule) with the exception that two surfactants, polysorbate 40 and poloxamer 188 were added in step 1 along with PEG 400 and PEG 1000. The encapsulation weight is 480 mg.

EXAMPLE 4

25 mg/Capsule: Oral Formulation at 5% Drug Loading

|  | (% w/w) | per capsule (mg) | 20,000 capsule batch (g) |
|---|---|---|---|
| active ingredient | 5.49 | 25.00 | 500.00 |
| Inactive Ingredients: |  |  |  |
| PEG 1000, NF | 32.66 | 148.61 | 2,972.16 |
| Povidone, USP K-17 (Plasdone C-15, ISP) | 10.55 | 48.00 | 960.00 |
| Polysorbate 80, NF | 10.55 | 48.00 | 960.00 |
| BHT, NF | 0.09 | 0.42 | 8.32 |
| BHA, NF | 0.91 | 4.16 | 83.2 |
| PEG 400, NF[2] | Q.S. to 100 | Q.S. to 455.00 | Q.S. to 9,100 g |

The formulation of Example 4 is produced in the same manner as that of 50 mg/capsule, above, with the exception that the heating temperature to solubilize the active ingredient in step 3 is 115±5° C., instead of 120±5° C. The encapsulation weight is 455 mg.

EXAMPLE 5

100 mg/Capsule: Oral Formulation at 15% Drug Loading

|  | (% w/w) | per capsule (mg) | 20,000 capsule batch (g) |
|---|---|---|---|
| active ingredient | 15.38 | 100.00 | 2,000.00 |
| Inactive Ingredient: |  |  |  |
| PEG 1000, NF | 28.98 | 188.35 | 3,767.05 |
| Povidone USP K-17 (Plasdone C-15, ISP)[3] | 10.00 | 65.00 | 1,300.00 |
| Polysorbate 80, NF | 9.45 | 61.39 | 1,227.91 |
| BHT, NF | 0.08 | 0.53 | 10.64 |
| BHA, NF | 0.82 | 5.32 | 106.42 |
| PEG 400, NF | Q.S. to 100 | Q.S. to 650.00 | Q.S. to 13,000.00 |

This formulation is produced with the same steps as the 50 mg/capsule, above, with the exception that the heating temperature to solubilize the active ingredient in step 3 is 145±5° C., instead of 120±5° C. The encapsulation weight is 650 mg in size 0 hard gelatin capsule.

EXAMPLE 6

150 mg in Size 00 Capsule

|  | (% w/w) | per capsule (mg) | 20,000 capsule batch (g) |
|---|---|---|---|
| active ingredient | 16.48 | 149.97 | 2,999.36 |
| Inactive Ingredients: |  |  |  |
| PEG 1000, NF | 26.3 | 239.33 | 4,786.60 |
| Povidone USP K-17 (Plasdone C-15, ISP) | 15 | 136.50 | 2,730.00 |
| Polysorbate 80, NF | 9.32 | 84.81 | 1,696.24 |
| BHT, NF | 0.08 | 0.73 | 14.56 |
| BHA, NF | 0.81 | 7.37 | 147.42 |
| PEG 400, NF | Q.S. to 100 | Q.S. to 910.00 | Q.S. to 18,200.00 |

This formulation of Example 6 is produced with the same steps as that of 50 mg/capsule with the exception of the heating temperature to solubilize the active ingredient in step 3 is 150±5° C., instead of 145±5° C. The encapsulation weight is 910 mg in size 00 hard gelatin capsule.

The following specific Examples 7 through 11 shown in Table 1, below, can be formulated as described above to create formulations of 10% active ingredient with varying concentrations of PEG 400, PEG 1000, two PVP components with respective K values of 15 and 90, and a combination of BHA and BHT as an adjuvant component.

TABLE 1

| Example No. | PEG 400 (%) | PEG 1000 (%) | PVP K15 (%) | PVP K90 (%) | BHT (%) | BHA (%) | NATC (%) | Active Ingred. (%) |
|---|---|---|---|---|---|---|---|---|
| 7 | 55.40 | 20.00 | 10.00 | 0.00 | 0.20 | 2.00 | 2.40 | 10.00 |
| 8 | 40.40 | 35.00 | 10.00 | 0.00 | 0.20 | 2.00 | 2.40 | 10.00 |
| 9 | 75.40 | 0.00 | 5.00 | 5.00 | 0.20 | 2.00 | 2.40 | 10.00 |
| 10 | 65.40 | 10.00 | 0.00 | 10.00 | 0.20 | 2.00 | 2.40 | 10.00 |
| 11 | 40.40 | 35.00 | 5.00 | 5.00 | 0.20 | 2.00 | 2.40 | 10.00 |

Similarly, the following Examples 12 through 32 may be formulated by the herein using PEG 400, PEG 1000, PVP with a K value of 17, active ingredient, BHA and BHT as antioxidants or preservatives and the additional components listed as "other".

TABLE 2

| Ex. No. | PEG 400 | PEG 1000 | PVP K-17 | Active Ingred. | BHA | BHT | Other | Other |
|---|---|---|---|---|---|---|---|---|
| 12 | 40.40 | 35.00 | 10.00 | 10.00 | 2.00 | 0.20 | Sodium Taurocholate 2.40 | — |
| 13 | 75.40 | — | 5.00 | 10.21 | 2.00 | 0.20 | Sodium Taurocholate 2.40 | PVP K-90 5.00 |
| 14 | 42.59 | 35.00 | 10.00 | 10.21 | 2.00 | 0.20 | — | — |
| 15 | 34.35 | 28.23 | 10.00 | 10.21 | 2.00 | 0.20 | Poloxamer 188 15.00 | — |
| 16 | 42.59 | 20.00 | 10.00 | 10.21 | 2.00 | 0.20 | Poloxamer 188 15.00 | — |
| 17 | 37.10 | 30.49 | 10.00 | 10.21 | 2.00 | 0.20 | Poloxamer 188 10.00 | — |
| 18 | 35.72 | 29.36 | 10.00 | 10.21 | 2.00 | 0.20 | Poloxamer 188 12.50 | — |
| 19 | 34.35 | 28.23 | 10.00 | 10.21 | 2.00 | 0.20 | Poloxamer 188 15.00 | — |
| 20 | 37.10 | 30.49 | 10.00 | 10.21 | 2.00 | 0.20 | Poloxamer 188 10.00 | — |
| 21 | 34.35 | 28.23 | 10.00 | 10.21 | 2.00 | 0.20 | Poloxamer 188 15.00 | — |
| 22 | 35.72 | 29.36 | 10.00 | 10.21 | 2.00 | 0.20 | Poloxamer 188 12.50 | — |
| 23 | 36.86 | 30.30 | 10.00 | 10.64 | 2.00 | 0.20 | Pluronic L44 10.00 | — |
| 24 | 36.86 | 30.30 | 10.00 | 10.64 | 2.00 | 0.20 | Pluronic L101 10.00 | — |
| 25 | 39.61 | 32.55 | 10.00 | 10.64 | 2.00 | 0.20 | Tween 40 5.00 | — |
| 26 | 41.25 | 33.91 | 10.00 | 10.64 | 2.00 | 0.20 | Tween 40 2.00 | — |
| 27 | 39.61 | 32.55 | 10.00 | 10.64 | 2.00 | 0.20 | Tween 20 5.00 | — |
| 28 | 41.25 | 33.91 | 10.00 | 10.64 | 2.00 | 0.20 | Tween 20 2.00 | — |
| 29 | 34.12 | 28.04 | 10.00 | 10.64 | 2.00 | 0.20 | Tween 40 5.00 | Poloxamer 188 10.00 |
| 30 | 36.86 | 30.30 | 10.00 | 10.64 | 2.00 | 0.20 | Tween 40 | — |
| 31 | 36.86 | 30.30 | 10.00 | 10.64 | 2.00 | 0.20 | Tween 80 10.00 | — |
| 32 | 34.12 | 28.04 | 10.00 | 10.64 | 2.00 | 0.20 | Tween 80 5.00 | Poloxamer 188 10.00 |

What is claimed:

1. A composition comprising:
   a) from about 1% to about 20% of a surfactant component;
   b) from about 55% to about 93% of a component of one or more polyethylene glycols (PEG) with an average molecular weight range of from about 190 to about 3450; and
   c) from about 1% to about 25% of one or more sucrose fatty acid esters or polyvinylpyrrolidone with a K value between about 15 and about 90, or a combination of one or more sucrose fatty acid esters or polyvinylpyrrolidone with a K value between about 15 and about 90.

2. A composition of claim 1 comprising:
   a) from about 5% to about 12% of a surfactant component;
   b) from about 60% to about 85%, of a component of one or more polyethylene glycols with an average molecular weight range of from about 400 to 1540; and
   c) from about 5% to about 15% of one or more sucrose fatty acid esters or polyvinylpyrrolidone (PVP) with a K value between about 15 and about 90, as defined in USP/NF, or a combination of one or more sucrose fatty acid esters or PVP.

3. A composition of claim 1 wherein the surfactant component comprises polysorbate 20, polysorbate 60, polysorbate 40, polysorbate 80, Span 80 Sorbitan Oleate, polysorbate 81, polysorbate 85, polysorbate 120, sodium taurocholates, sodium deoxytaurocholates, chenodeoxycholic acid, ursodeoxycholic acid, pluronic or poloxamers, or combinations thereof.

4. A composition of claim 1 wherein the component of one or more polyethylene glycols comprises a mixture of PEG 400 and PEG 1000 in a ratio of between about 2.5:1 to about 1:2.5.

5. A composition of claim 1 wherein the polyvinylpyrrolidone component has a K value of about 17.

6. A composition of claim 1 further comprising a component of from about 0.1% to about 4% of one or more antioxidants or preservatives.

7. A composition of claim 6 wherein the one or more antioxidants or preservatives are selected from ascorbyl palmitate, benzyl alcohol, butylated hydroxyanisole, or butylated hydroxytoluene, or combinations thereof.

8. A composition of claim 7 wherein the one or more antioxidants or preservatives comprise about 0.3% to about 2.5% butylated hydroxyanisole and from about 0.005% to about 0.15% butylated hydroxytoluene.

9. A composition comprising:
   a) from about 1% to about 20% of a surfactant component;

b) from about 55% to about 93% of a component of one or more polyethylene glycols (PEG) with an average molecular weight range of from about 190 to about 3450;

c) from about 1% to about 25% of one or more sucrose fatty acid esters or polyvinylpyrrolidone with a K value between about 15 and about 90, or a combination of one or more sucrose fatty acid esters or polyvinylpyrrolidone with a K value between about 15 and about 90; and d) a component of from about 0.1% to about 4% of one or more antioxidants or preservatives.

10. A composition of claim 9 wherein the one or more antioxidants or preservatives are selected from ascorbyl palmitate, benzyl alcohol, butylated hydroxyanisole, or butylated hydroxytoluene, or combinations thereof.

11. A composition of claim 9 wherein the surfactant component comprises polysorbate 20, polysorbate 60, polysorbate 40, polysorbate 80, Span 80 Sorbitan Oleate, polysorbate 81, polysorbate 85, polysorbate 120, sodium taurocholates, sodium deoxytaurocholates, chenodeoxycholic acid, ursodeoxycholic acid, pluronic or poloxamers, or combinations thereof.

12. A composition of claim 9 wherein the one or more antioxidants or preservatives are selected from ascorbyl palmitate, benzyl alcohol, butylated hydroxyanisole, or butylated hydroxytoluene, or combinations thereof.

13. A composition comprising:

a) from about 32% to about 36% of PEG 1000;

b) from about 35% to about 46% PEG 400;

c) from about 9% to about 14% of povidone;

d) from about 9% to about 14% Polysorbate 80;

e) from about 0.005% to about 0.02% butylated hydroxytoluene; and f) from about 0.5% to about 2.0% butylated hydroxyanisole.

14. A composition of claim 13 comprising:

a) from about 33% to about 35% of PEG 1000;

b) from about 37.5% to about 43% PEG 400;

c) from about 10.5% to about 13% Polysorbate 80;

d) from about 0.075% to about 0.015% butylated hydroxytoluene;

e) from about 0.75% to about 1.5% butylated hydroxyanisole; and f) from about 10.0% to about 13% of povidone.

* * * * *